United States Patent [19]

Hall et al.

[11] 4,145,510
[45] Mar. 20, 1979

[54] 5-SUBSTITUTED PHOSPHONATE HYDANTOINS AND DERIVATIVES THEREOF

[75] Inventors: Luther A. R. Hall, Woodcliff Lake, N.J.; David A. Gordon, Scarsdale, N.Y.

[73] Assignee: Ciba-Geigy Corporation, Ardsley, N.Y.

[21] Appl. No.: 885,059

[22] Filed: Mar. 9, 1978

Related U.S. Application Data

[62] Division of Ser. No. 698,623, Jun. 21, 1976, Pat. No. 4,093,809.

[51] Int. Cl.² .............................................. C08G 18/38
[52] U.S. Cl. .................. 528/72; 260/45.7 P; 260/45.8 N; 260/830 TW; 521/165; 528/287; 528/367; 548/309; 548/310; 548/312; 548/313
[58] Field of Search .......................................... 528/72

[56]         References Cited

U.S. PATENT DOCUMENTS

| | | | |
|---|---|---|---|
| 2,381,121 | 8/1945 | Ericks ..................... | 544/204 |
| 2,861,079 | 11/1958 | Britton et al. ........................ | 542/442 |
| 3,629,263 | 12/1971 | Batzer et al. ...................... | 260/309.5 |
| 3,821,243 | 6/1974 | Habermeier et al. ............. | 260/309.5 |
| 3,892,765 | 7/1975 | Porret et al. ...................... | 260/309.5 |
| 3,920,685 | 11/1975 | Porret et al. ...................... | 260/309.5 |
| 3,925,406 | 12/1975 | Porret et al. ...................... | 260/309.5 |
| 3,946,034 | 3/1976 | Porret et al. ...................... | 260/309.5 |
| 3,971,813 | 7/1976 | Porret et al. ...................... | 260/309.5 |
| 3,978,076 | 8/1976 | Porret et al. ...................... | 260/309.5 |

OTHER PUBLICATIONS

Lyons, *The Chemistry & Use of Wine Retardants*, Wiley-Interscience, NY, 1970, pp. 20-24. Chem. Abstr. 69, 78116m, 1968.
Chem. Abstr. 47, 4837b, 1953.
Chem. Abstr. 52, 3713d, 1958.
Harvey, *Tetrahedron* 22, 1966, pp. 2561-2573.
Dawson et al., J. Am. Chem. Soc. 74, 1952, pp. 5312-5314.
Cotton et al., J. Am. Chem. Soc. 85, 1963, pp. 2402-2406.
Chem. Abstr. 50, 11230f, 1956.
Jacobson et al., J. Am. Chem. Soc. 79, 1957, pp.2608-2612.
Buchi et al., J. Am. Chem. Soc. 92, 1970, pp. 3126-3133.
Habermeier, Angew. Makromol. Chem. 35, 1974, pp. 9-25.
Chem. Abstr. 80, 121680q, 1974.

*Primary Examiner*—M. J. Welsh
*Attorney, Agent, or Firm*—Luther A. R. Hall

[57]                ABSTRACT

Hydantoins of the formula

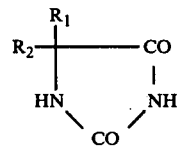

wherein $R_1$ is hydrogen or alkyl of 1 to 8 carbon atoms, $R_2$ is

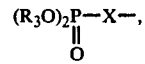

$R_3$ is alkyl of 1 to 8 carbon atoms, and X is a straight or branched chain alkylene of 1 to 4 carbon atoms or a straight or branched chain alkylene of 3 to 6 carbon atoms containing an internal carbamido group; or $R_1$ and $R_2$ together are Y where Y is a straight or branched chain alkylene of 4 to 8 carbon atoms having a pendant

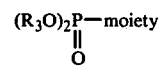

are prepared by reacting first α,β-unsaturated aldehydes or ketones with alkyl phosphites to form a phosphonate aldehyde or ketone followed by a classical Bucherer hydantoin synthesis.

4 Claims, No Drawings

5-SUBSTITUTED PHOSPHONATE HYDANTOINS AND DERIVATIVES THEREOF

This is a divisional of application Ser. No. 698,623 filed on June 21, 1976, now U.S. Pat. No. 4,093,809 issued on June 6, 1978.

BACKGROUND OF THE INVENTION

The present invention pertains to hydantoins substituted in the 5-position by phosphonate containing moieties. These materials are useful as starting materials for preparing flame-retardant polymers particularly epoxy resins, polyesters and polyurethanes.

It has long been known that the incorporation of phosphorus compounds, halogenated compounds, antimony oxide and nitrogen compounds into organic systems imparts varying degrees of flame retardancy thereto depending on the chemical nature of the flame retardant and the organic system being made flame retardant. This subject is reviewed in depth in "The Chemistry and Use of Fire Retardants," J. W. Lyons, Wiley-Interscience, New York, 1970.

Phosphorus is particularly efficacious as a flame retardant in the presence of nitrogen. There often appears to be synergism between these elements with the presence of nitrogen often reducing the need for high amounts of phosphorus, (Lyons, ibid, pp 20-24) to achieve an acceptable level of flame retardancy. Such a combination would exist with the phosphonate hydantoins of the present invention which contain both pendant phosphonate groups and nitrogen molecules in the hydantoin ring.

That such a combination might provide salubrious flame retardant properties in polymeric systems is seen in the teachings of the prior art whereby a variety of reactions hydantoin molecules are substituted in the 3-position by a phosphonate containing moiety as seen in U.S. Pat. Nos. 3,892,765; 3,920,685; and 3,925,406. These prior art hydantoins have only one free —NH— group available for later glycidylation. The monoglycidyl phosphonate hydantoins described therein are useful as low smoke generating flame retardants for epoxy resin systems, but the heat distortion properties of such resin systems are somewhat lower than unmodified epoxy resin systems due to the monofunctionality of these monoglycidyl phosphonate hydantoins. These hydantoins are monofunctional and therefore lead to less highly cross linked resins than do the phosphonate hydantoins of the present invenion. These monoglycidyl phosphonate hydantoins also lead to resin systems with much greater water sensitivity than the resins derived from the phoshonate hydantoins of this invention.

The prior art in U.S. Pat. No. 3,946,034 teaches that hydantoins substituted in the 3-positon by a phosphonate containing moiety may form adducts with polyglycidyl compounds which in turn can be used to form epoxy resins having desirable flame retardant properties. The heat distortion temperatures of the epoxy resins formed, however, are still somewhat lower than for unmodified epoxy resins.

In Swiss Pat. No. 456,949 it is taught that dialkyl phosphites can react with polyepoxides to yield reaction products which when cured form moderately flame-retardant epoxy resins. However, the reaction of dialkyl phosphites with epoxides takes place incompletely even with long reaction times.

In U.S. application, Ser. No. 404,835 filed Oct. 9, 1973, now U.S. Pat. No. 3,971,813 oligomeric adducts of polyglycidyl hydantoins with dialkyl phosphites are used to prepare flame-retardant epoxy resins having good heat distortion temperature properties. The structure of the adducts involved require some interaction or transesterification between the phosphite molecule and the glycidyl groups and thus have phosphorus atoms in some polymer chains. The instant compounds have pendant phosphonate groups.

DETAILED DISCLOSURE

This invention pertains to new hydantoins substituted in the 5-position by phosphonate containing moieties, a process for their manufacture, methods of using said hydantoins as starting materials for preparing intermediates useful in the manufacture of flame-retardant epoxy resins, polyesters and polyurethanes, and also the flame-retardant polymers prepared therefrom.

The new hydantoins have the general formula

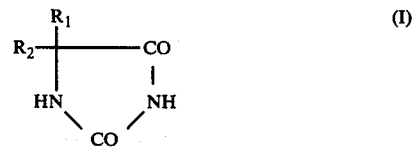

wherein $R_1$ is hydrogen or alkyl of 1 to 8 carbon atoms, $R_2$ is

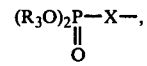

$R_3$ is alkyl of 1 to 8 carbon atoms and X is a straight or branched chain alkylene of 1 to 4 carbon atoms or a straight or branched chain alkylene of 3 to 6 carbon atoms containing internal carbamido group, or $R_1$ and $R_2$ together are Y where is a straight or branched chain alkylene of 4 to 8 carbon atom having a pendant

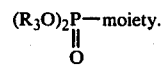

$R_1$ can be hydrogen or alkyl of 1 to 8 carbon atoms such as methyl, ethyl, n-butyl, isoamyl, n-hexyl and n-octyl. Preferably $R_1$ is hydrogen, methyl or ethyl. Most preferably $R_1$ is hydrogen or methyl.

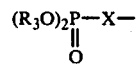

where $R_3$ can be alkyl of 1 to 8 carbon atoms such as methyl, ethyl, isopropyl, sec-butyl, n-hexyl and n-octyl. Preferably $R_3$ is methyl or ethyl. Most preferably $R_3$ is ethyl. The ethyl esters are preferred over the methyl esters for their greater hydrolytic stability. Although the hydantoins where $R_3$ is alkyl of 3 to 8 carbon atoms are effective flame retardants, there is no advantage gained in having $R_3$ being alkyl higher than ethyl since such additional molecular weight dilutes unnecessarily the phosphorus and nitrogen contents of the structure. Phosphorus and nitrogen moieties provide the flame retardant properties to the hydantoins and their derivatives.

X is a straight or branched chain alkylene of 1 to 4 carbon atoms such as methylene, ethylene, —C(CH$_3$)$_2$CH$_2$—, —CH(CH$_3$)CH$_2$— and —CH$_2$CH(CH$_3$)—. Preferably X is ethylene or —C(CH$_3$)$_2$CH$_2$—.

X can also be a straight or branched chain alkylene of 3 to 6 carbon atoms containing an internal carbamido group such as —CH$_2$CONHCH$_2$CH$_2$—, —CH$_2$CONHC(CH$_3$)$_2$CH$_2$—, —CH$_2$CH$_2$CONHCH$_2$CH$_2$— and —CH$_2$CH$_2$CONHC(CH$_3$)$_2$CH$_2$—. Preferably X is —CH$_2$CH$_2$CONHC(CH$_3$)$_2$CH$_2$—.

Y is a straight or branched chain alkylene of 4 to 8 carbon atoms having a pendant

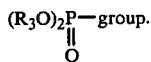 group.

Y can be

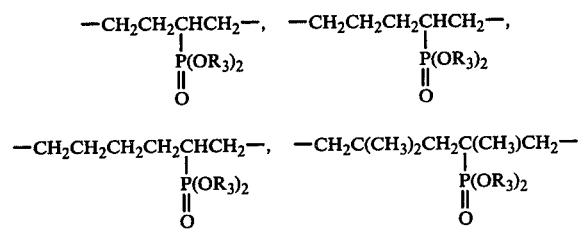

and the like.
Preferably Y is

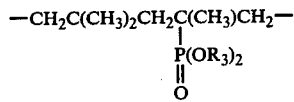

Of particular interest are compounds of formula I wherein R$_1$ is hydrogen or methyl, R$_2$ is

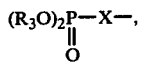

R$_3$ is ethyl and X is ethylene or —C(CH$_3$)$_2$CH$_2$—, or R$_1$ and R$_2$ together are Y where Y is

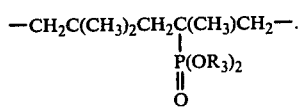

Among these most preferred embodiments, the compound of special interest for reasons of economy and product efficacy is the material of formula I wherein R$_1$ is methyl, R$_2$ is

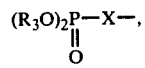

R$_3$ is ethyl and X is —C(CH$_3$)$_2$CH$_2$—.

Also of interest are compounds where R$_1$ is hydrogen, methyl or ethyl, R$_2$ is

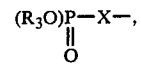

R$_3$ is methyl or ethyl, and X is ethylene, —C(CH$_3$)CH$_2$— or —CH$_2$CH$_2$CONH(CH$_3$)$_2$CH—; or R$_1$ and R$_2$ together are Y where Y is

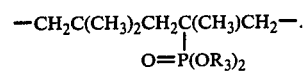

Examples of individual compounds of formula I are the following 5-substituted phosphonate hydantoins:
5-diethylphosphonomethyl-5-methylhydantoin
5-(2-di-n-butylphosphonoethyl)-5-ethylhydantoin
5-(2-di-n-octylphosphonoethyl)-5-isoamylhydantoin
5-(2-dimethylphosphonopropyl)hydantoin
5-(1-methy-2-diisopropylphosphonoethyl)hydantoin
di-n-butyl 7,9,9-trimethyl-1,3-diazaspiro[4.5]-decane-2,4-dione-7-ylphosphonate
diethyl 1,3-diazaspiro[4.4]nonane-1,4-dione-7-ylphosphonate
dimethyl 1,3-diazaspiro[4.6]undecane-2,4-dione-7-ylphosphonate Methods of Preparation The hydantoins of this invention can be prepared by known methods including the classic Bucherer synthesis with potassium or sodium cyanide, ammonium carbonate and a phosphonate ketone or aldehyde. The phosphonate hydantoin so formed can be then glycidylated in the usual fashion with epichlorohydrin and alkali or converted into a diol by reaction with an alkylene oxide.

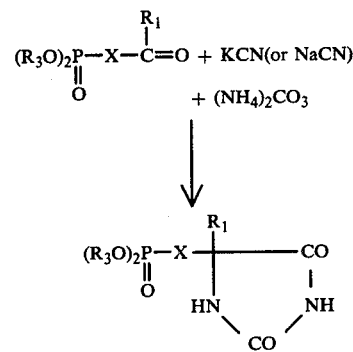

R$_1$, R$_3$ and X are as defined above.

The phosphonate ketone or aldehyde can be prepared by one of several routes as seen below.

1. Dialkyl phosphite plus an $\alpha,\beta$-unsaturated ketone or aldehyde

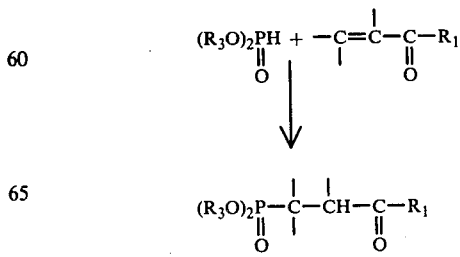

A. N. Pudovik, *Zh. Obshch. Khim.*, 22, 1371 (1952); *Chem. Abst.*, 47, 4837 (1953); A. N. Pudovik, *Zh. Obshch. Khim.*, 27, 1617 (1957); *Chem. Abst.*, 52, 3713 (1958).

Examples of commercially available α,β-unsaturated ketones are methyl vinyl ketone, ethyl vinyl ketone, mesityl oxide, methyl isopropenyl ketone, isophorone, 3-penten-2-one, 2-cyclopenten-1-one, 2-cyclohexen-1-one and 2-cyclohepten-1-one. Such ketones can be manufactured by known methods, for example by condensation of the appropriate methyl ketones with aldehydes or ketones. For reasons of availability and cost, mesityl oxide is preferred. Other α,β-unsaturated ketones useful in this invention include α-ionone, β-ionone, 4-methoxy-3-buten-2-one and phorone.

Examples of commercially available α,β-unsaturated aldehydes are acrolein, methacrolein and crotonaldehyde. Other α,β-unsaturated aldehydes useful in this invention include 2-hexanal, cinnamaldehyde and α-methylcinnamaldehyde.

The phosphites are known compounds of industrial availability. Examples thereof are dialkyl phosphites, such as dimethyl, diethyl or dioctyl phosphite, and mixed phosphites, such as methyl butyl phosphite.

2. Trialkyl phosphite plus α,β-unsaturated ketone or aldehyde to yield a mixture of desired carbonyl compound plus corresponding dialkyl ketal or acetal followed by acid hydrolysis of the mixture to the desired phosphonate ketone or aldehyde.

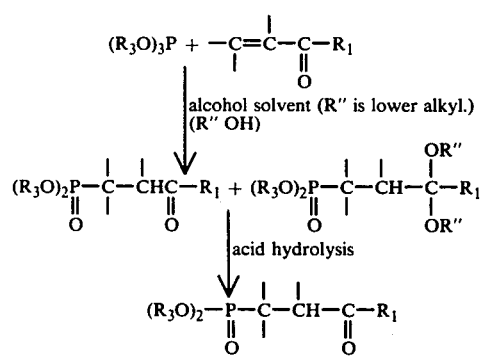

$R_3$ and $R''$ may be the same or different.

R. G. Harvey, *Tetrahedron*, 22, 2561 (1966).

The trialkyl phosphites such as triethyl phosphite, trimethyl phosphite, tri-n-butyl phosphite as well as mixed trialkyl phosphites are available commercially.

3. Arbuzov reaction of trialkyl phosphite and a reactive halide (Hal = chlorine, bromine or iodine)

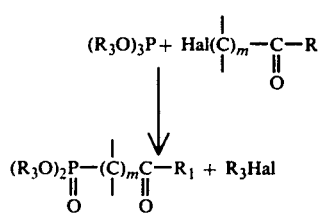

where m is 1, 2, 3 or 4.

N. D. Dawson and A. Burger, *J. Am. Chem. Soc.*, 74, 5312 (1952); F. A. Cotton and R. A. Schunn, Ibid, 85, 2400 (1963).

The reactive halides useful in this prodedure include chloroacetone, 1-chloro-3-pentanone, 5-chloro-2-pentanone and the like which are in many cases available commercially.

An alternative procedure for the preparation of the phosphonate hydantoins of this invention involves the addition of a dialkyl phosphite to a preformed 5,5-alkylidenehydantoin. These are prepared, for example, by condensation of hydantoin with aldehydes (U.S. Pat. No. 2,861,079).

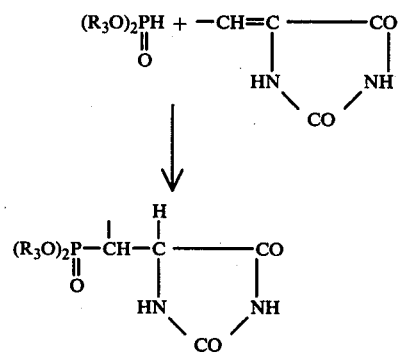

The phosphonate hydantoins of this invention are generally monohydantoins which can be converted into diglycidyl derivatives by reaction with epichlorohydrin and alkali as seen in Examples 1–8.

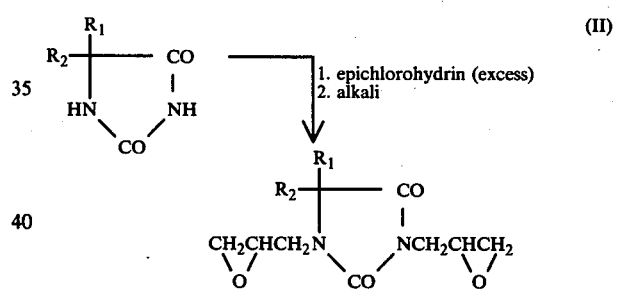

$R_1$ and $R_2$ are defined as in formula I.

However, phosphonate hydantoins of this invention which are bishydantoins and which have a glycidyl functionality of over two can also be made as seen in Example 9.

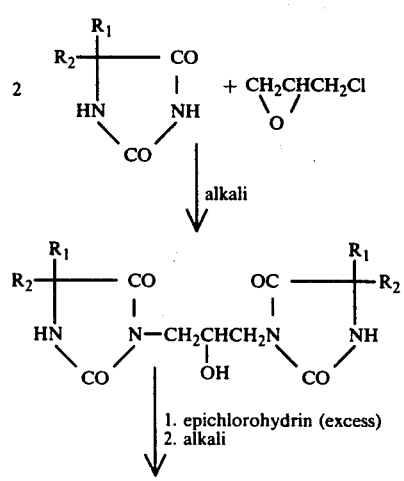

-continued

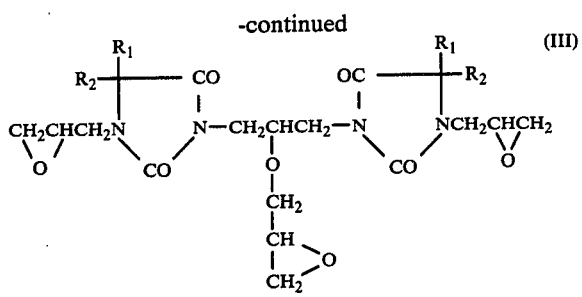

$R_1$ and $R_2$ are defined as in formula I

Such triglycidyl phosphonate hydantoins can also be incorporated into epoxy resin systems to impart low smoke, flame retardancy. The higher functionality provides increased crosslink density after cure in such epoxy systems with a concomitant improvement in rigidity, heat distortion temperature and related physical properties with good flame retardant properties as seen in Example 10. Related good storage-stable hydantoin triglycidyl compounds not having pendant phosphonate moieties are depicted in U.S. Pat. No. 3,821,243.

A particularly useful triglycidyl compound of formula III is prepared in Example 9 where $R_1$ is methyl and $R_2$ is 2-diethylphosphono-2-methylpropyl.

The phosphonate hydantoins of this invention can also be converted by reacting with alkylene oxides, preferably ethylene oxide, as seen in Example 11 into phosphorus containing diols. Such diols are useful as polymer intermediates in preparing flame-retardant polyesters or polyurethanes. Hydantoin moieties, not having any pendant phosphonate groups, are reacted with oxiranes to form hydantoins containing pendant hydroxyalkyl groups according to the teachings of U.S. Pat. No. 2,831,121 and 3,629,263.

A particularly useful diol compound of formula IV is prepared in Example II wherein $R_1$ is methyl, $R_2$ is 2-diethylphosphono-2-methylpropyl and $R_4$ is hydrogen.

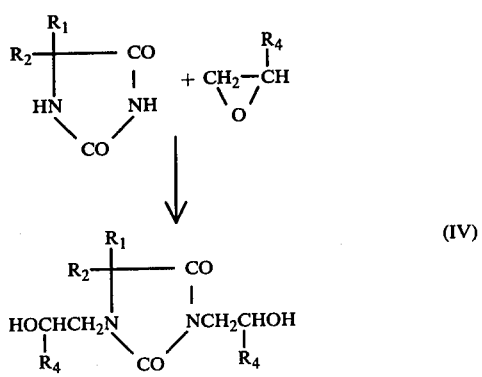

$R_1$ and $R_2$ are as defined in formula I, $R_4$ is hydrogen, methyl or ethyl, but preferably hydrogen.

The above diols may be retracted with diacids, dimethyl esters of diacids such as dimethyl terephthalate and other polyester intermediates to form flame retardant polyesters having pendant phosphonate moieties providing the desirable flame retardant properties.

The diols may also be reacted with diisocyanates as seen in Example 12 to form flame retardant polyurethanes having the unit structural formula V.

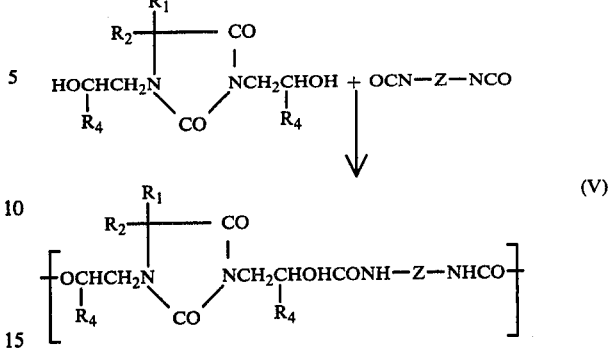

where $R_1$, $R_2$ and $R_4$ are as defined above and where Z is a difunctional organic radical such as alkylene of 4 to 10 carbon atoms, phenylene, xylylene, tolylene, $-C_6H_4CH_2C_6H_4-$, $-C_6H_{10}CH_2C_6H_{10}-$ and the like derived from the wide variety of diisocyanates available in commerce. Of particular interest are the polyurethanes where $R_1$, $R_2$ and $R_4$ are the preferred and most preferred embodiments described above and where Z is alkylene of 4 to 6 carbon atoms, tolylene, xylylene, $-C_6H_4CH_2C_6H_4-$ or $-C_6H_{10}CH_2C_6H_{10}-$. Particularly preferred are the polyurethanes where $R_1$ is methyl, $R_2$ is 2-diethylphosphono-2-methylpropyl, $R_4$ is hydrogen and Z is $-C_6H_4CH_2C_6H_4-$ or $-C_6H_{10}CH_2C_6H_{10}-$.

Utility

The hydantoins of formula I and more particularly the glycidylated hydantoins of this invention are flame retardant, low smoke generating components for polymer systems especially epoxy resins when the final system preferably contains between 3 and 4% phosphorus. Flame retardance is bestowed to some degree to the system when the phosphorus content is as low as 0.8%. There is increasing need for plastic and polymeric structures in the electrical, building, construction, aerospace and related industries which are not only flame retardant, but which do not emit large quantities of smoke when under thermal excitation. Mandated government regulations on aircraft interiors for safety reasons emphasize the need for such products.

The epoxy resins made from the glycidylated phosphonate hydantoins of this invention are non-corrosive to the environment especially electrical components for expensive computers and the like. Brominated resins are corrosive when thermally degraded yielding noxious and toxic gases.

However, for such flame retardant and low smoke polymers to be useful in practice, the tensile strength, elongation, modulus, heat distortion temperature, flexural strength, impact strength, deflection value, water absorption level and other physical properties must not be deleteriously affected compounds to the unmodified polymer system involved.

The use of difunctional phosphonate hydantoin intermediates leads to epoxy polymer systems with superior physical properties essentially the same, except for the desired flame retardancy and low smoke properties, as normal epoxy resin systems whereas the use of the monofunctional glycidyl phosphonate cyclic ureides described in the cited prior art cases may lead to reduced physical properties in some cases.

The glycidylated phosphonate hydantoins of this invention may be substituted directly in the epoxy resin formulation for the normal glycidylated components which lack phosphorus. The amount of instant compound that is needed depends on its phosphorus content. While epoxy resins having as little as 0.8% by weight phosphorus exhibit desirable flame retardant properties, epoxy resins having about 3% phosphorus content by weight exhibit excellent low smoke, flame retardancy. Depending on the exact formulation involved the weight percent of the glycidylated phosphonate hydantoins of this invention to be used in epoxy formations to achieve flame retardancy ranges from 15 to 100%, preferably from 40 to 60%.

In addition to the flameproofing agents of this invention, it is also possible to add to the polymeric substrates other flameproofing agents. e.g., organic halogen compounds, antimony oxide or other phosphorus compounds.

It is furthermore possible to add other customary and known additives, e.g., antioxidants, heat stabilizers, UV absorbers, fluorescent brighteners, antistatic agents, lubricants, softeners, emulsifiers, pigments, carbon black, asbestos, kaolin, talcum, glass fibers or other fillers and reinforcing agents.

The following examples are presented for the purpose of illustration only and are not to be construed to limit the nature or scope of the instant invention in any manner whatsoever.

It is noted that with some hydantoins of this invention diastereoisomers are possible because of the asymmetry of the chemical structures involved. The utility of these compounds as flame retardant additives or intermediates for polymeric systems is not adversely affected whether a pure diastereoisomer or whether a mixture of said isomers is employed. In such cases a mixture of isomers would normally be used for reasons of convenience and economy.

EXAMPLE 1

1,3-Diglycidyl-5-(2-diethyl-phosphonoethyl)-5-methylhydantoin a. Diethyl 3-Oxobutylphosphonate To 243 grams (1.76 moles) of diethyl phosphite stirred under nitrogen and protected by a drying tube was added a solution of sodium ethoxide prepared from 5.07 grams (0.22 mole) of sodium in 100 ml of anhydrous ethanol. Methyl vinyl ketone, 112 grams (1.60 moles), was then added at such a rate as to keep the temperature at 35°–40° C. The addition required about one hour. The reaction mixture was stirred for one-half hour after the addition was completed and was stripped to dryness in vacuo at 60° C./16 mm. The residue was taken up in 600 ml of chloroform, and the solution cooled to 15° C. and washed successively with dilute acid, water and saturated sodium chloride solution. After drying, the chloroform solution was distilled to yield 112 grams of diethyl 3-oxobutylphosphonate as a colorless liquid, B.P. 106° C./0.05 mm, $n_D25$ 1.4340. VPC indicated that the product was 90% pure.

b. 5-(2-Diethylphosphonoethyl)-5-methylhydantoin

A mixture of 208 grams (1 mole) of diethyl 3-oxobutylphosphonate, 130 grams (2 moles) of potassium cyanide, and 456 grams (4.75 moles) of ammonium carbonate dissolved in 2200 ml of 50:50 ethanol-water was heated and stirred under nitrogen at reflux for five hours. After the heating period, the reaction mixture was stripped in vacuo at 70° C./16 mm and the residue dried at 75° C./0.1 mm. Anhydrous ethanol, 1100 ml, was added to the residue and the mixture boiled until only inorganic salts remained undissolved. The suspension was cooled and then filtered. The clear filtrate was cooled to 5°–10° C. and anhydrous hydrogen chloride was bubbled in until the mixture had a pH of about 2. The resulting turbid solution was warmed at 40°–50° C. with 25 grams of charcoal and refiltered. The ethanol solution was then heated in vacuo to give a viscous syrup, 246 grams. The crude syrup was recrystallized from ethyl acetate to give a white crystalline product in a yield of 145 grams (52% of theory), m.p. 100°–103° C.

Analysis: Calc'd for $C_{10}H_{19}N_2O_5P$: C, 43.17; H, 6.88; N, 10.07; P, 11.13. Found: C, 42.95; H, 6.77; N, 10.09; P, 11.12.

The NMR and IR spectra were consistent for the assigned structure.

c. 1,3-Diglycidyl-5-(2-diethylphosphonoethyl)-5-methylhydantoin

A mixture of 139 grams (0.5 mole) of 5-(2-diethylphosphonoethyl)-5-methylhydantoin, 925 grams (10 moles) of epichlorohydrin, and 3.0 grams (0.02 mole) of tetramethylammonium chloride (TMAC) was heated to 80°–95° C. and maintained at that temperature for two hours. As the reaction mixture was warmed initially, an exothermic reaction occurred at 55° C. which carried the temperature to 95° C. without external heating. At the end of the 2-hour heating period, the reaction mixture was cooled to 60° C. and at a vacuum of about 120 mm, 100 grams (1.25 moles) of 50% aqueous sodium hydroxide solution was added over a period of 1.5 hours. During this time a continuous circulatory distillation was carried out in which the azeotroped water was collected and the epichlorohydrin was returned to the reaction flask. The distillation was carried on for 15 minutes after the addition was complete, and the reaction mixture was then filtered hot to remove precipitated sodium chloride. The clear filtrate was stripped of excess epichlorohydrin in vacuo. The crude syrup was purified by dissolving in chloroform and washing with saturated sodium chloride solution. After removal of the chloroform in vacuo, a yield of 151 grams (77% of theory) of the desired glycidylated hydantoin ws obtained as a clear, pale yellow, viscous syrup.

Analysis: Calc'd for $C_{16}H_{27}N_2O_7P$: P, 7.93; Cl, 0.00. Found: P, 7.75; 7.68; Cl, 0.60, 0.79.

Epoxide Equivalent/Kg: Calc'd: 5.11. Found: 5.25, 5.28.

The NMR spectrum was consistent for the assigned structure.

EXAMPLE 2

1,3-Diglycidyl-5-methyl-5-(2-diethylphosphono-2-methylpropyl)hydantoin a. 5-Methyl-5-(2-diethylphosphono-2-methylpropyl)hydantoin A suspension of 23.6 grams (0.1 mole) of diethyl 1,1-dimethyl-3-oxobutylphosphonate [A. N. Pudovick, *Zh. Obshch. Khim.*, 22, 1371 (1952)], 40 ml of ethanol, 30 ml of water, 9.8 grams (0.15 mole) of potassium cyanide and 28.8 grams (0.3 mole) of powdered ammonium carbonate was heated at 60° C. for six hours. The reaction mixture was cooled and filtered to remove suspended salts. The filtrate was neutralized with hydrochloric acid, and evaporated to dryness. Residual inorganic salts were removed by dissolving the residue in methylene chloride and followed by filtration. The product was then isolated by evaporation of the solvent and drying to yield 19.5 grams (64%) of 5-methyl-5-(2-diethylphosphono-2-methylpropyl)hydantoin, m.p. 142°–146° C. Recrystallization from ethyl acetate raised the m.p. to 146°–148.5° C.

Analysis: Calc'd for $C_{12}H_{23}N_2O_5P$: C, 47.06; H, 7.57; N, 9.15; P, 10.11. Found: C, 46.90; H, 7.53; N, 9.08; P, 10.24.

The NMR spectrum was consistent with the assigned structure.

b. One pot process for preparation of 5-methyl-5-(2-diethylphosphono-2-methylpropyl)-hydantoin To a mixture of 829 grams (6 moles) of diethyl phosphite and 589 grams (6 moles) of mesityl oxide contained in a 12 liter three-necked flask fitted with stirrer, thermometer and powder funnel was gradually added a solution of 81.6 grams (1.2 moles) of sodium ethoxide in 400 grams of ethanol with water bath cooling, over a period of 8 minutes. The addition reaction was strongly exothermic and the reaction mixture reached a peak temperature of 130° C. during the period. The reaction mixture was cooled to 30° C., then the following reagents were added: 1730 grams (18 moles) of powdered ammonium carbonate, 2000 ml of ethanol, 469 grams (7.2 moles) of potassium cyanide and 2400 ml of distilled water. The resulting suspension as heated to 56° C. over a period of 90 minutes and at 56° C. for an additional 7 hours. After cooling to room temperature, the reaction mixture consisting of two liquid phases was diluted with 2000 ml of chloroform, stirred and allowed to settle. The top organic phase was separated and concentrated by distillation at reduced pressure, finally at 115° C. at 30 mm Hg, leaving 1545 grams (84%) of the desired hydantoin phosphonate as a clear orange syrup. The hot syrup was dissolved in 2800 ml of ethyl acetate. After crystallization overnight at 0° C., the crystalline product was filtered, washed with 2500 ml of cold ethyl acetate and dried, yielding 990 grams (54%) of pure 5-methyl-5-(2-diethylphosphono-2-methylpropyl)-hydantoin, m.p. 147.5°–148° C.

c. 1,3-Diglycidyl-5-methyl-5-(2-diethylphosphono-2-methylpropyl)hydantoin

A mixture of 306.3 grams (1 mole) of 5-methyl-5-(2-diethylphosphono-2-methylpropyl)hydantoin, 1.5 grams of tetramethylammonium chloride and 2360 ml of epichlorohydrin was heated at reflux of 90 minutes. The reaction mixture was cooled to 60° C., then 176 grams (2.2 moles) of 50% aqueous sodium hydroxide solution was added dropwise to the reaction mixture with stirring over a 75-minute period. At the same time water was distilled off azeotropically at 60° C./120 mm Hg and epichlorohydrin from the distillate was continuously recycled into the reaction flask. The mixture was heated for an additional 45 minutes at 60° C., filtered hot and excess epichlorohydrin was distilled off at reduced pressure. The residue was taken up in methylene chloride and the solution was filtered through a magnesium sulfate pad. Evaporation of solvents, finally at 65° C./0.1 mm Hg, furnished 364 grams (87%) of 1,3-diglycidyl-5-methyl-5-(2-diethylphosphono-2-methylpropyl)hydantoin as an amber syrup.

Analysis: Calc'd for $C_{18}H_{31}N_2O_7P$: C, 51.67; H, 7.47; N, 6.69; P, 7.40; Cl, none. Found: C, 50.72; H, 7.61; N, 6.38; P, 6.94; Cl, 0.75.

Epoxide Content: Calc'd: 4.78 eg/kg. Found: 4.68 eg/kg (97.9% of theory).

EXAMPLE 3

1,3-Diglycidyl-5-methyl-5-(6-diethylphosphono-2,2-dimethyl-3-aza-4-oxohexyl)hydantoin a. N-(1,1-Dimethyl-3-oxobutyl)-2-diethylphosphonoacrylamide

Using the same procedure of Example 1 for the preparation of diethyl 3-oxobutylphosphonate, a solution prepared from the reaction of 3.1 grams (0.135 mole) of sodium with 63 ml of anhydrous ethanol was added under nitrogen and drying conditions with stirring at room temperature to 152 grams (1 mole) of diethyl phosphite. To this solution was then added over a one hour period maintaining the internal temperature at 30°–40° C. with external cooling, 169 grams (1 mole) of diacetone acrylamide. The solution was then stirred for another hour at 24° C. before 8.2 grams (0.135 mole) of acetic acid was slowly added to bring the pH to 5. The solution was dried at 70° C./16 mm and topped off by distillation for 30 minutes with a maximum pot temperature of 120° C. at 0.2 mm. The pot residue (316 grams) was the desired N-(1,1-dimethyl-3-oxybutyl)-2-diethylphosphonoacrylamide in a 97% yield. Structure of the desired product with a purity of about 95% was confirmed by NMR.

b. 5-Methyl-5-(6-diethylphosphono-2,2-dimethyl-3-aza-4-oxohexyl)hydantoin

To a stirred solution of 316 grams (0.97 mole) of N-(1,1-dimethyl-3-oxobutyl-2-diethylphosphonoacrylamide (taken as 95% pure for stoichiometry purposes) in 2500 ml of 50% aqueous ethanol was added under nitrogen in 139.4 grams (2.0 moles) of potassium cyanide and 456 grams (4.75 moles) of ammonium carbonate. The mixture was refluxed with stirring for 7.5 hours, with 4 hours at a solution temperature of 80° C. The solution was then stripped of solvents at 80° C./16 mm to yield an oil which was treated with 1200 ml of ethanol until all the oil dissolved and a granular solid remained. This mixture was filtered, and the filtrate was then acidified to pH 2 with anhydrous hydrogen chloride. The solution was treated with Filter Cel, refiltered and stripped of solvents in a rotary evaporator at 70° C./16 mm and then at 85° C./0.3 mm for 1 hour to yield 283 grams (78%) of 5-methyl-5-(6-diethylphosphono-2,2-dimethyl-2-aza-4-oxohexyl)hydantoin as a tacky solid. The structure was confirmed by NMR.

Analysis: Calc'd for $C_{15}H_{28}N_3O_6P$: P=8.21. Found: P=8.81.

c. 1,3-Diglycidyl-5-methyl-5-(6-diethylphosphono-2,2-dimethyl-3-aza-4-oxohexyl)hydantoin To a solution of 283 grams (0.78 mole) of 5-methyl-5-(6-diethylphosphono-2,2-dimethyl-3-aza-4-oxohexyl)-hydantoin in 1387.5 grams (15 moles) of epichlorohydrin under nitrogen and stirring was added 4.16 grams (0.04 mole) of TMAC, tetramethylammonium chloride catalyst. The temperature was slowly raised to 80° C. Stirring was continued for 1.75 hours maintaining the temperature at 80° C. Then 209.8 grams (2.62 moles) of 50% aqueous sodium hydroxide was added over a one-hour period at 70° C./120 mm while water was removed continuously from the reaction mixture by azeotropic distillation and the heavier epichlorohydrin phase of the distillate was returned to the reaction vessel. Distillation was continued for another 15 minutes and the mixture was then filtered hot. The filtrate was cooled and refiltered through magnesium sulfate filter cake. The resultant filtrate was stripped of solvents at 80° C./16 mm and then for several hours at 90° C./16 mm and then for several hours at 90° C./0.05 mm to yield 342 grams (90%) of 1,3-diglycidyl-5-methyl-5-(6-diethylphosphono-2,2-dimethyl-3-aza-4-oxohexyl)-hydantoin.

Analysis: Calc'd for $C_{21}H_{36}N_3O_8P$: C, 51.53; H, 7.41; N, 8.58; P, 6.33; Cl, 0. Found: C, 49.42; H, 7.58; N, 7.56; P, 5.85; Cl, 1.66.

Expoxy Equivalent/Kg: Calc'd: 4.09. Found: 3.74.

The structure of the hydantoin product was confirmed by NMR.

EXAMPLE 4

Diethyl 7,9,9-Trimethyl-1,3-diglycidyl-1,3-diazaspiro[4.5]decane-2,4-dione-7-ylphosphonate (two diastereoisomers)

a. Diethyl 7,9,9-Trimethyl-1,3-diazaspiro[4.5]decane-2,4-dione-7-ylphosphonate

A suspension of 829 grams (3 moles) of diethyl 3-oxo-1,5,5-trimethylcyclohexylphosphonate (A. N. Pudovik and I. V. Konovalova, *Zh, Obshch. Khim.*, 27, 1617 (1957), 293 grams (4.5 moles) of potassium cyanide, and 864 grams (9 moles) of powdered ammonium carbonate in 1200 ml of ethanol and 900 ml of water, was heated to 55° C. with stirring over a period of 30 minutes. The mixture was heated at 55° C. for an additional 5.5 hours, cooled to room temperature and filtered through a Buchner funnel. The resulting two diastereomeric hydantoin derivatives (isomers A and B) which differ in solubilities and melting points were then isolated, respectively, from the filter cake and filtrate.

The white filter cake was washed thoroughly with 6000 ml of water, sucked dry and dried in vacuum oven at 70° C. for two days furnishing 682 grams of crude hydantoin derivative. The product was triturated with 2600 ml of boiling ethyl acetate, filtered, and dried at 75° C. in a vacuum oven overnight, yielding 572 grams (55%) of a pure spirohydantoin phosphonate, isomer A, m.p. 271°–272° C.

Analysis: Calc'd for $C_{15}H_{27}N_2O_5P$: C, 52.02; H, 7.86; N, 8.09; P, 8.94. Found: C, 51.95; H, 8.22; N, 7.99; P, 9.26.

The assigned structure was fully supported by the NMR spectrum.

To isolate the other isomer, B, the filtrate from the original reaction mixture was concentrated on a rotary evaporator. The precipitated solid was filtered, washed neutral with water and dried for two days at 70° C. in a vacuum oven, yielding 250 grams (24%) of a tan colored crystalline material, m.p. 171°–179° C. Recrystallization from 1300 ml of ethyl acetate afforded 190 grams of spirohydantoinphosphonate, isomer B, m.p. 177°–180° C.

Analysis: Calc'd for $C_{15}H_{27}N_2O_5P$: C, 52.02; H, 7.86; N, 8.09; P, 8.94. Found: C, 52.00; H, 8.08; N, 8.00; P, 8.99.

The NMR spectrum was consistent for the assigned structure.

b. Diethyl 7,9,9-Trimethyl-1,3-diglycidyl-1,3-diazaspiro[4,5]-decane-2,4-dione-7-ylphosphonate A mixture of 173 grams (0.5 mole) of the spirohydantoin phosphonate isomer B, 0.5 grams of tetramethylammonium chloride and 1390 grams (15 moles) of epichlorohydrin was heated at 95° C. for 90 minutes. The resulting clear colorless solution was cooled to 60° C., and over a period of one hour, 88 grams of a 50% aqueous sodium hydroxide solution was added dropwise. During the addition of the aqueous sodium hydroxide solution, the water in the reaction mixture was continuously removed by azeotropic distillation with epichlorohydrin at ca. 125 mm Hg pressure. After phase separation of the distillate, the heavier epichlorohydrin phase was continuously returned to the reaction flask. The reaction mixture was further heated for 45 minutes at 60° C. at 100 mm Hg. The hot reaction mixture was filtered. The filtrate was concentrated on a rotary evaporator to remove excess epichlorohydrin. To remove traces of suspended salts, the residue was dissolved in 700 ml of chloroform and filtered through a super-cel pad.

Removal of solvents after 4 hours at 65° C./0.2 mm Hg yielded 212 grams (92%) of the N,N'-diglycidyl derivative as an amber viscous resin.

Analysis: Calc'd for $C_{21}H_{35}N_2O_7P$: C, 55.01; H, 7.69; N, 6.11; P, 6.76; Cl, none. Found: C, 54.80; H, 7.64; N, 6.09; P, 6.52; Cl, 0.57.

Epoxide Content: Calc'd: 4.36 eq/Kg. Found: 4.26 eq/Kg (97.7% of theory).

EXAMPLE 5

1,3-Diglycidyl-5-(2-diethylphosphonopropyl)-hydantoin (two diastereoisomers)

a. Diethyl 1-Methyl-3,3-diethoxypropylphosphonate

Ref: R. G. Harvey, *Tetrahedron*, 22, 2561 (1966).

To a solution of 175.3 grams (2.5 moles) of crotonaldehyde in 460.7 grams (10 moles) of ethanol stirred under nitrogen at 0° C. was added over a half hour period 415 grams (2.5 moles) of triethyl phosphite. The mixture was stirred for an additional hour at 0° C. and then allowed to warm up. An exotherm resulted raising the temperature to 50° C. The mixture was stirred at 50° C. for three hours and then refluxed at 85° C. for 20 hours. After removal of low boiling fractions at 85° C./16 mm, the residue was distilled to yield 402 grams (57%) of diethyl 1-methyl-3,3-diethoxypropyl-phosphonate as a colorless liquid boiling at 95°–112° C./0.25–0.35 mm. The structure was confirmed by IR and NMR.

b. Diethyl 1-Methyl-3-oxopropylphosphonate

A solution of 400 grams (1.42 moles) of diethyl 1-methyl-3,3-diethoxypropylphosphonate in 1 liter of water and 4 liters of acetone containing 30 ml of concentrated hydrochloric acid was stirred and refluxed under nitrogen at 62° C. for 1.5 hours. Low boiling materials were removed at 80° C./16 mm to give the diethyl 1-methyl-3-oxopropylphosphonate in a 296 grams (quantitative) yield as a pale yellow liquid. The structure was confirmed by NMR.

c. 5-(2-Diethylphosphonopropyl)hydantoin

A solution of 296 grams (1.42 moles) of diethyl 1-methyl-3-oxopropylphosphonate in 190 ml of water was brought to pH 3-4 using a 25% solution of sodium hydroxide. The resultant solution was added to a solution of 151.5 grams (1.46 moles) of sodium bisulfite dissolved in 985 ml of water and 644 ml of 2B ethanol. The mixture was stirred under nitrogen for 3.5 hours and then diluted with 825 ml of water and 1356 ml of ethanol. The resultant mixture was allowed to stand overnight at 5° C.

To the above solution of the bisulfite addition product of the phosphorus containing aldehyde was added 187.5 grams (2.88 moles) of potassium cyanide and 553.0 grams (5.76 moles) of ammonium carbonate. The resultant mixture was refluxed for 4 hours under nitrogen. After removing insoluble inorganic salts by filtration and the aqueous ethanol solvent in vacuo, the desired product was obtained in crude form as an oil. The oil was dissolved in 2 l of 2B ethanol and the pH adjusted to 2 with anhydrous hydrogen chloride. The resultant milky material was filtered and then heated at 80° C./16 mm and then 80° C./0.5 mm for 45 minutes to yield 382 grams of turbid oil containing the two diasteroisomers of the desired hydantoin along with an insoluble product containing phosphorus, but no nitrogen which was not further identified.

Analysis of this turbid oil showed it to contain roughly 60% of the two desired hydantoin stereoisomers.

Separation of these products was effected by dissolving 370 grams of this turbid oily product in 7 liters of ethyl acetate. The resulting mixture was filtered, with the filtrate then concentrated to a total volume of 1400 ml of refiltered hot to remove a brownish tar. One diastereoisomer of the desired product crystallized out of this ethyl acetate solution as a white crystalline product in a yield of 71 grams (19%) with a melting point of 158-161° C.

Analysis: Calc'd for $C_{10}H_{19}N_2O_5P$: C, 43.17; H, 6.88; N, 10.07; P, 11.13. Found: C, 43.28; H, 6.89; N, 10.12; P, 11.09.

The mother liquor above was evaporated at 70° C./16 mm and then 80° C./0.25 mm to yield 153.6 grams (40%) of a brownish oil containing a major portion of the other stereoisomer.

Analysis: Calc'd for $C_{10}H_{19}N_2O_5P$: C, 43.17; H, 6.88; N, 10.07; P, 11.13. Found: C, 43.38; H, 7.26; N, 8.73; P, 10.25.

The structure of these isomers were confirmed by NMR.

An alernate procedure to prepare the 5-(2-diethylphosphonopropyl)hydantoin involved the reaction of diethyl 1-methyl-3-oxopropylphosphonate directly with potassium cyanide and ammonium carbonate without going through the intermediate sodium bisulfite addition product. A mixture of 50 grams (0.28 mole) of diethyl 1-methyl-3-oxopropylphosphonate, 36 grams (0.56 mole) of potassium cyanide and 128.6 grams (1.34 moles) of ammonium carbonate in 500 ml of 50% aqueous ethanol was stirred and refluxed under nitrogen for 3.5 hours. The mixture was cooled, filtered and excess solvent removed under vacuum, finally at 70° C./0.25 mm. The residue was refluxed with 250 ml of ethanol, cooled and refiltered. The pH of the filtrate was adjusted to pH 2 with anhydrous hydrogen chloride. The resultant solution was evaporated in vacuo to yield a heavy syrup which was then dissolved in 500 ml of ethyl acetate and refiltered. The filtrate was stripped to a volume 100 ml and 11.8 grams (15%) of the white crystalline diastereoisomer of 5-(2-diethylphosphonopropyl)-hydantoin was obtained (MP = 115-159° C.). The structure was confirmed by NMR. The mother liquor was evaporated at 80° C./0.25 mm to yield 33 grams (42%) of a brown oil which was shown by NMR to be a mixture of two stereoisomers of 5-(2-diethylphosphonopropyl)hydantoin.

d. 1,3-Diglycidyl-5-(2-diethylphosphonopropyl)hydantoin.

A mixture of 60 grams (0.22 mole) of 5-(2-diethylphosphonopropyl)hydantoin, 400 grams (4.3 moles) of epichlorohydrin and 1.3 grams (0.01 mole) of tetramethylammonium chloride was stirred and heated for 2 hours at 80° C. after an initial exotherm raised the temperature from 50 to 95° C. Circular distillation was begun at 70° C./150 mm and 43.2 grams (0.54 mole) of 50% aqueous sodium hydroxide was added over a 30 minute period. Distillation was continued for another 15 minutes. The mixture was filtered hot and then stripped of solvents at 70° C./16 mm and then at 80° C./0.25 mm for 1 hour to yield 70 grams (81%) of 1,3-diglycidyl-5-(2-diethylphosphonopropyl)hydantoin as a light yellow syrup.

Analysis: Calc'd for $C_{16}H_{27}N_2O_7P$: P, 7.94; cl, none. Found: P, 7.00; Cl, 2.24.

Epoxy Equivalent gm/Equiv. Calc'd: 196. Found: 224.

The structure was confirmed by NMR.

EXAMPLE 6

1,3-Diglycidyl-5-methyl-5-diethylphosphonomethylhydantoin

When using the procedure of Example 1 the 5-(2-diethylphosphonoethyl)-5-methylhydantoin is replaced by an equimolar amount of 5-methyl-5-diethylphosphonomethylhydantoin, the above named product is obtained.

5-Methyl-5-diethylphosphonomethylhydantoin is prepared from diethyl 2-oxopropylphosphonate which in turn is made by any of several methods including the Arbuzov reaction of triethyl phosphite with bromoacetone [A. N. Pudovik, *Doklady Akad Nauk, SSSR*, 105, 735 (1955)]of with iodoacetone [H. I. Jacobson, et al, *J. Amer. Chem. Soc.*, 79, 2608 (1957)]or by the reaction of diethyl methylphosphonate, butyl lithium in tetrahydrofuran and ethyl acetate (56% yield) [G. Buchi and J. E. Powell, Jr., *J. Amer. Chem. Soc.*, 92, 3126 (1960)]. The melting point of 5-methyl-5-diethylphosphonomethylhydantoin is 122-124° C.

EXAMPLE 7

1,3-Diglycidyl-5-(2-diethylphosphonoethyl)hydantoin

When using the procedure of Example 5 the 5-(2-diethylphosphonopropyl)hydantoin is replaced by an equimolar amount of 5-(2-diethylphosphonoethyl)hydantoin, the above named product is obtained.

Following the procedure of Example 5, the 5-(2-diethylphosphonoethyl)hydantoin is prepared from diethyl 3-oxopropylphosphonate which in turn is the hydrolysis product of diethyl 3,3-diethoxypropylphosphonate made by the reaction of acrolein and triethyl phosphite.

EXAMPLE 8

1,3-Diglycidyl-5-(1-methyl-2-diethylphosphonoethyl)-hydantoin (two diastereoisomers)

When using the procedure of Example 5 the 5-(2-diethylphosphonopropyl)hydantoin is replaced by an equivalent amount of 5-(1-methyl-2-diethylphosphonoethyl)hydantoin, the above named product is obtained.

Following the procedure of Example 5, the 5-(1-methyl-2-diethylphosphonoethyl)hydantoin is prepared from diethyl 2-methyl-3-oxopropylphosphonate which in turn is the hydrolysis product of diethyl 2-methyl-3,3-diethyoxypropylphosphonate made by the reaction of triethyl phosphite and methacrolein.

EXAMPLE 9

1,3-Bis-[1-glycidyl-5-methyl-5-(2-diethylphosphono-2-methylpropyl)hydantoin-3-yl]propyl-2-glycidyl ether Ref: J. Habermeier, *Angew, Makromol Chem.*, 35, 9 (1974).

In a one liter round bottom flask equipped with stirrer, addition funnel, condenser and thermometer was placed 60 ml of water at 75° C. and 118.0 grams (0.38 mole) of 5methyl-5-(2-diethylphosphono-2-methylpropyl)hydantoin of Example 2a. To the resulting colorless solution was added 15.2 grams of 50% aqueous sodium hydroxide solution (0.19 mole) over a period of 35 minutes which the temperature was maintained at 75° C. The reaction mixture was heated to 85° C. and 17.6 grams (15 ml) of epichlorohydrin (0.19 mole) was added over a 45 minute period. At 72° C. an additional 140 ml of epichlorohydrin was then added over 15 minutes. After settling the aqueous phase was removed and discarded. The organic phase was dried by distilling off an azeotropic mixture of epichlorohydrin and water at 60° C./100 mm Hg with continuous return of the epichlorohydrin to the reaction vessel over a 45 minute period. To the resulting mixture was added 2 grams of 50% aqueous solution of tetramethylammonium chloride and the mixture stirred for one hour at 90° C. Then 54.7 grams of 50% aqueous sodium hydroxide (0.68 mole) was added gradually over a 25 minute period at 55–60° C. while water was continuously removed from the system by azeotropic distillation at ca 100 mm Hg. Azetropic distillation with recycling of epichlorohydrin was continued for one additional hour at which time the distillate was clear. The suspension was filtered hot through super-cel and magnesium sulfate layers and the solution evaporated at 100° C. at reduced pressure. The residual viscous yellowish syrup was dried further on the rotary evaporator at 100° C., 0.5 mm Hg for four hours yielding 116.1 grams (73%) of a glassy resin.

Analysis: Calc'd for $C_{36}H_{62}N_4O_{14}P_2$: C, 51.68; H, 7.47; N, 6.69; P, 7.40; Cl, none. Found: C, 50.59; H, 7.50; N, 6.58; P, 7.03; Cl, 0.49.

Epoxide Equivalent: Calc'd: 3.59 eg/kg. Found: 3.57 eq/kg (>99% of theory).

The NMR Spectrum in DMSO-$d_6$ was consistent for the assigned structure and indicated no impurities.

EXAMPLE 10

Preparation of a Casting from the Triglycidyl bis(hydantoin) phosphonate of Example 9

To 100 parts by weight of the triglycidyl bis(hydantoinphosphonate) of Example 9 was added 49.5 parts of hexahydrophthalic anhydride and 2 parts of benzyldimethylamine. The mixture was then curved at 90° C. for 18 hours and at 150° C. for 2 hours. A specimen cut from this casting exhibited an oxygen index of 34.2 as determined by ASTM D2863-70.

EXAMPLE 11

1,3-Di-(β-hydroxyethyl)-5-methyl-5-(2-diethylphosphono-2-methylpropyl)hydantoin In a three-liter, three-necked flask equipped with stirrer, thermometer and Dry-Ice condenser was dissolved 306.3 grams (1 mole) of 5-methyl-5-(2-diethylphosphono-2-methylpropyl)hydantoin of Example 2a and 4.25 grams of lithium chloride in 900 ml of N,N-dimethylformamide, by stirring at room temperature for 45 minutes.

Then a solution of 132.1 grams (3 moles) ethylene oxide in 700 ml of N,N-dimethylformamide (prepared by bubbling the gas into the solvent with ice bath cooling and stirring until the weight gain corresponded to the desired quantity) was added all at once. The reaction mixture was then heated gradually from 20 to 90° C. over a 1 hour period and subsequently for an additional 2.5 hours at 88° C. After standing overnight most of the solvent was distilled off at 65° C. and reduced pressure. The residue (415 grams) was dissolved in 2000 ml of chloroform and washed with 300 ml of water. The organic phase was separated, dried overnight over 175 grams of molecular sieves type 4A, stripped of solvents and dried at 65° C. 0.3 mm for 3 hours on a rotary evaporator yielding 364.8 grams (92.5%) of the product as a pale yellowish viscous syrup.

Analysis: Calc'd for $C_{16}H_{31}N_2O_7P$: C, 48.72; H, 7.92; N, 7.10. Found: C, 48.85; H, 8.30; N, 7.33.

EXAMPLE 12

Preparation of a Polyurethane from the Diol of Example 11

A 500 ml resin kettle was charged with 60.0 grams of 1,3-di(β-hydroxyethyl)-5-methyl-5-(2-diethylphosphono-2-methylpropyl)-hydantoin of Example 11, 34.04 grams of diphenylmethane-4,4'-diisocyanate, 0.3 gram of triethylenediamine, 0.3 gram of dibutyltin diacetate, and 400 ml of N,N-dimethylformamide. The reaction mixture was heated at 115° C. for 1.5 hours, after which time there were no detectable residual isocyanate groups present as seen by absence of isocyanate absorption in the infrared spectrum. The hot reaction mixture was poured into 3 l of cold water with stirring. The precipitate was filtered and dispersed repeatedly in water in a blender, finally filtered and dried in a vacuum oven at 70° C. for 3 days at reduced pressure. The product weighed 92.0 grams (93.6%), softened at 134° C. and had a phosphorus content of 2.9%. Gel permeation chromatography showed a peak molecular weight of 10,000.

When the diphenylmethane-4,4'-diisocyanate was replaced by an equivalent amount of 4,4'-methylenebis(-cyclohexylisocyanate) using the general procedure above, the corresponding polyurethane was prepared from the diol of Example 11.

EXAMPLES 13 to 23

Flameproofing of Epoxy Resins

Several epoxy resin formulations were prepared with and without the glycidylated phosphonate hydantion compound of this invention. Controls using other flame retardant systems were also run. The physical properties, flammability and smoke generation data on the cured resin specimens prepared from said formulations are given on Table I. The effectiveness of the glycidylated phosphonate hydantoins in conferring good flame retardancy and preventing undue smoke generation while maintaining very acceptable physical properties in the cured epoxy resin samples is clearly demonstrated.

The quanity of glycidylated phosphonate hydantoin needed in these epoxy formulations to impart good flame retardancy and to repress smoke generation varies from about 40 to 60 weight percent of the total formulation depending on their inherent phosphorus content. The higher that phosphorus content, the less of the glycidylated phosphonate hydantoin is needed to reach to approximately 3% total phosphorus content in the final epoxy formulation found to impart good flame retardancy to epoxy systems.

Formulations were prepared based on a desired phosphorus level of about 3 weight percent phosphorus in total resin/hardener/accelerator/additive system. Experimentally determined phosphorus levels for these additives were used in the calculations. The amount of hardener used was determined as a ratio of equivalents of hardener to the epoxide equivalent of the base resin plus additive. The ratios used are indicated on Table I.

Accelerator was added on the basis of one part per hundred parts resin plus additive.

All samples were prepared in 3-necked round-bottomed flasks. The base resin, additive, and hardener were weight in first. These were stirred in vacuo at temperature (from 25–60° C.) to achieve thorough mixing and remove dissolved gases. When the system was degassed, accelerator was added and the system stirred in vacuo to degas further. The resin mixture was then carefully poured into aluminum molds to form $4 \times 5 \times \frac{1}{4}''$ and $4 \times 5 \times \frac{1}{8}''$ ($10.16 \times 12.7 \times 0.635$ cm and $10.16 \times 12.7 \times 0.317$ cm) plaques. All physical tests were made on samples cut from these plaques. The curing schedule listed on the data sheets is broken down as follows:

| Cure Schedule: | | |
|---|---|---|
| Processing | 60° C, 15 min. | total stirring and degassing time and temperature; |
| Gelling | 100° C, 16 hrs. | Gelling time and temperature; |
| Postcure | 150° C, 2 hrs. | final cure time and temperature. |

TABLE I

| | | Example 13 | Example 14 | Example 15 | Example 16 | Example 17 | Example 18 |
|---|---|---|---|---|---|---|---|
| Formulations* (parts by weight) | | | | | | | |
| Glycidylated Phosphonate Hydantoin of Example | | — | 1 | 2 | 3 | 4 | 5 |
| Glycidylated Phosphonate Hydantoin Amount | | — | 42.5 | 47.2 | 56.1 | 50.3 | 42.5 |
| Epoxy Resin ARALDITE 6010 | | 55.2 | 13.1 | 10.7 | 6.7 | 9.5 | 13.1 |
| Liquid Anhydride Hardener | | 44.2 | 43.8 | 41.5 | 36.6 | 39.6 | 43.8 |
| Benzyldimethylamine | | 0.6 | 0.6 | 0.6 | 0.6 | 0.6 | 0.6 |
| Phosphorus Content of Formulation (% by weight) | | None | 3.3 | 3.3 | 3.3 | 3.3 | 3.3 |
| Cure | | | | | | | |
| Processing | ° C/min | 100/15 | 60/15 | 60/15 | 60/10 | 60/10 | 60/15 |
| Gelling | ° C/hrs | 100/17 | 100/16 | 80/17 | 80/17 | 80/18 | 80/17 |
| Postcure | ° C/hrs | 150/2 | 150/2 | 150/2 | 150/2 | 150/2 | 150/2 |
| Physical Properties (at 25° C) | | | | | | | |
| Flexural Strength | (psi $\times 10^{-3}$) | 15.5 | 9.9 | 15.0 | 17.0 | 7.5 | 16.0 |
| Flexural Modulus | (psi $\times 10^{-3}$) | 430 | 424 | 435 | 488 | 427 | 450 |
| Tensile Strength | (psi $\times 10^{-3}$) | 10.4 | 5.1 | 8.2 | 9.4 | 8.3 | 9.0 |
| Tensile Modulus | (psi $\times 10^{-3}$) | 368 | — | 409 | 400 | 421 | 415 |
| Elongation | (%) (at 25° C) | 7.6 | — | 3.0 | 3.9 | 2.8 | 3.0 |
| Flammability Characteristics | | | | | | | |
| Limiting Oxygen Index | | 19.4 | 32.8 | 29.0 | 23.2 | 29.0 | 31.5 |
| Flame Spread | | UL100 | $UL_{10}^0$(94VE-1) | $UL_5^0$(94VE-0) | $UL_{15}^5$(burns) | $UL_5^0$(94VE-0) | $UL_5^0$(94VE-0) |
| Smoke | | Not Avail. | 1 | 1 | 1 | 1 | — |
| Heat Distortion Temp. ° C (264 psi) | | 119 | 112 | 109 | 105 | 115 | 114 |
| Water Absorption (% after 24 hrs) | | 0.08 | 0.48 | 1.52 (7 days) | 0.89 | 0.36 | 0.60 |

| | | Example 19 | Example 20 | Example 21 | Example 22 | Example 23 |
|---|---|---|---|---|---|---|
| Formulations* (parts by weight) | | | | | | |
| 1-Glycidyl Phosphonate Hydantoin of (see footnote) | | a | b | c | d | Brominated Epoxy Resin |
| 1-Glycidyl Phosphonate Hydantoin Amount | | 39.2 | 50.9 | 45.2 | 51.1 | 29.9 |
| Epoxy Resin ARALDITE 6010 | | 24.2 | 16.6 | 20.0 | 15.0 | 32.4 |
| Liquid Anhydride Hardener | | 36.1 | 31.8 | 34.2 | 33.2 | 37.1 |
| Benzyldimethylamine | | 0.5 | 0.7 | 0.7 | 0.7 | 0.6 |
| Phosphorus Content of Formulation (% by weight) | | 3.4 | 3.3 | 3.3 | 3.3 | 15% Bromine |
| Cure | | | | | | |
| Processing | ° C/min | 60/15 | 60/15 | 60/15 | 70/15 | 100/15 |
| Gelling | ° C/hrs | 100/17 | 100/20 | 100/17 | 100/20 | 100/18 |
| Postcure | ° C/hrs | 150/2 | 150/2 | 150/2 | 150/2 | 150/2 |
| Physical Properties (at 25° C) | | | | | | |
| Flexural Strength | (psi $\times 10^{-3}$) | 12.5 | 13.9 | 11.2 | 12.9 | 10.2 |
| Flexural Modulus | (psi $\times 10^{-3}$) | 485 | 509 | 477 | 531 | 452 |
| Tensile Strength | (psi $\times 10^{-3}$) | 9.5 | — | 9.8 | 7.4 | 10.5 |
| Tensile Modulus | (psi $\times 10^{-3}$) | — | — | 445 | 382 | — |
| Elongation | (%) (at 25° C) | — | — | 2.8 | 2.3 | — |
| Flammability Characteristics | | | | | | |
| Limiting Oxygen Index | | 28.2 | 26.2 | 27.0 | 27.0 | 27.4 |
| Flame Spread | | $UL_5^0$(94VE-1) | UL100 | $UL_5^0$(94VE-0) | $UL_5^0$(94VE-0) | $UL_{10}^5$(94VE-1) |

TABLE I-continued

| | | | | | |
|---|---|---|---|---|---|
| Smoke | 2 | 2 | 1 | 1 | 3 |
| Heat Distortion Temp °C (264 psi) | 68 | 91 | 70 | 70 | 129 |
| Water Absorption (% after 24 hrs) | 0.52 | 0.21 | 0.30 | 0.97 | — |

Footnotes to TABLE I
*Formulations
Epoxy Resin ARALDITE 6010, commercially available from CIBA-GEIGY Corporation
1 - glycidyl derivative of phosphonate hydantoin of
a. Example 2, U.S. Patent 3,925,406
b. dimethylphosphono analogue of Example 3, U.S. Patent 3,925,406
c. Example 3, U.S. Patent 3,925,406
d. Example 7, U.S. Patent 3,892,765
Brominated Epoxy Resin is ARALDITE LT8049, commercially available from CIBA-GEIGY Corporation.
Liquid Anhydride hardener is ARALDITE 917, commercially available from CIBA-GEIGY Corporation.
Test procedures are:
Flexural Strength according to ASTM D790
Flexural Modulus according to ASTM D790
Tensile Strength according to ASTM D638
Tensile Modulus according to ASTM D638
Elongation according to ASTM D638
Limiting Oxygen Index according to ASTM D2863-FO. General Electric Flammability Gauge was used for all tests. The Limiting Oxygen Index indicates the minimum oxygen content in a nitrogen-oxygen mixture at which the test specimen just still continues to burn.
Flame Spread according to Underwriter's Laboratories, Inc. "UL94" (tests for flammability of plastic materials).
"UL94" vertical burinig test was used for all cases unless marked otherwise. 94VE ratings are used where applicable. $UL_b{}^a$ ratings are an indication of the time the sample burned where:
a = average time (in seconds) to self-extinguish after first lighting (rounded to the nearest 5 seconds)
b = average time (in seconds) to self-extinguish after second lighting (rounded to nearest 5 seconds)
Smoke - a qualitative scale of 0 to 3 was adopted for use during the Flame Spread tests where 0 is no smoke visible, 1 is light smoke, 2 is medium smoke and 3 is heavy smoke.
Heat Distortion Temperature according to ASTM D648
Water Absorption according to ASTM D570
To convert psi $\times 10^{-3}$ values to Kg/cm$^2$ units multiply by 70.

A comparison of the physical properties seen on Table I for the epoxy resin without any flame retardant and for epoxy resin containing the diglycidyl phosphonate hydantoins of this invention are essentially the same in all important aspects including especially retention of good heat distortion temperature values. Significant increases in the oxygen index values and the low smoke values indicate greatly enhanced flame retardancy in epoxy systems containing the diglycidyl phosphonate hydantoins of this invention. Water absorption values were slightly higher than for the unmodified control, but still well within the acceptable range of useful properties.

When the diglycidyl phosphonate hydantoins of this invention are compared to a commercial brominated epoxy resin used as a flame retardant for epoxy systems, similar physical properties and oxygen index values were obtained. The brominated resin gave rise to an objectionable amount of acrid smoke on ignition whereas the phosphonate hydantoins provided comparable flame retardancy with the generation of only low amounts of smoke.

When the digylcidyl phosphonates of this invention are compared to the 1-glycidyl-3-dialkylphosphono-substituted hydantoins of U.S. Pat. Nos. 3,892,765; 3,925,406; and 3,920,685 in these epoxy systems, all these materials provide good flame retardancy, low smoke generation and most physical properties. However, the diglycidyl phosphonates hydantoins provide far superior heat distortion temperature values than do the monoglycidyl phosphonate hydantoins.

What is claimed is:

1. A flame resistant polyurethane having the unit structural formula V

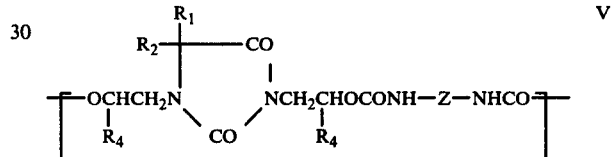

wherein $R_1$ is hydrogen or alkyl of 1 to 8 carbon atoms, $R_2$ is

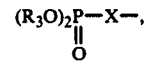

$R_3$ is alkyl of 1 to 8 carbon atoms, X is a straight or branched chain alkylene of 1 to 4 carbon atoms or a straight or branched chain alkylene of 3 to 6 carbon atoms containing an internal carbamido group, or $R_1$ and $R_2$ together are Y where Y is a straight or branched chain alkylene of 4 to 8 carbon atoms having a pendant

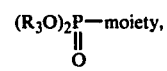

$R_4$ is hydrogen, methyl or ethyl, and Z is alkylene of 4 to 10 carbon atoms, phenylene, tolylene, xylylene —C$_6$H$_4$CH$_2$C$_6$H$_4$— or —C$_6$H$_{10}$CH$_2$C$_6$H$_{10}$—.

2. A polyurethane according to claim 1 wherein $R_1$ is hydrogen, methyl or ethyl, $R_2$ is

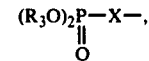

$R_3$ is methyl or ethyl, X is ethylene, —C(CH$_3$)$_2$CH$_2$ or —CH$_2$CH$_2$CONHC(CH$_3$)$_2$CH$_2$—, or $R_1$ and $R_2$ together are Y where Y is

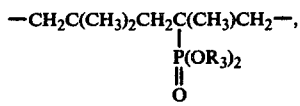

$R_4$ is hydrogen, and Z is alkylene of 4 to 6 carbon atoms, tolylene, xylylene, —$C_6H_4CH_2C_6H_4$— or —$C_6H_{10}CH_2C_6H_{10}$—.

3. A polyurethane according to claim 1 wherein $R_1$ is hydrogen or methyl, $R_2$ is

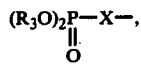

$R_3$ is ethyl, X is ethylene or —$C(CH_3)_2CH_2$—, or $R_1$ and $R_2$ together are

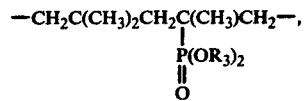

$R_4$ is hydrogen, and Z is —$C_6H_4CH_2C_6H_4$— or —$C_6H_{10}CH_2C_6H_{10}$—.

4. A polyurethane according to claim 1 wherein $R_1$ is methyl, $R_2$ is

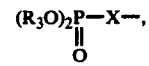

$R_3$ is ethyl, X is —$C(CH_3)_2CH_2$—, $R_4$ is hydrogen and Z is —$C_6H_4CH_2C_6H_4$— or —$C_6H_{10}CH_2C_6H_{10}$—.

* * * * *